United States Patent
Tzou et al.

(10) Patent No.: US 10,307,224 B2
(45) Date of Patent: Jun. 4, 2019

(54) ORTHODONTIC APPLIANCES WITH DISSOLVABLE COATINGS

(75) Inventors: Tsi-Zong Tzou, Arcadia, CA (US); Matthew T. Scholz, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 541 days.

(21) Appl. No.: 14/240,455

(22) PCT Filed: Aug. 14, 2012

(86) PCT No.: PCT/US2012/050717
§ 371 (c)(1),
(2), (4) Date: Feb. 24, 2014

(87) PCT Pub. No.: WO2013/028396
PCT Pub. Date: Feb. 28, 2013

(65) Prior Publication Data
US 2014/0212827 A1 Jul. 31, 2014

Related U.S. Application Data

(60) Provisional application No. 61/526,939, filed on Aug. 24, 2011.

(51) Int. Cl.
*A61C 7/14* (2006.01)

(52) U.S. Cl.
CPC ............... *A61C 7/146* (2013.01); *A61C 7/14* (2013.01)

(58) Field of Classification Search
CPC .. A61C 7/12; A61C 7/14; A61C 7/146; A61C 2201/002

(Continued)

(56) References Cited

U.S. PATENT DOCUMENTS 3,577,516 A * 5/1971 Gould et al. ...... A61F 13/00008
128/849
4,129,638 A * 12/1978 Ritze ................... A61K 8/0275
264/117

(Continued)

FOREIGN PATENT DOCUMENTS

| JP | 08-112293 A | 5/1996 |
|----|-------------|--------|
| JP | 2008-539022 | 11/2008 |
| WO | WO 2001-37789 | 5/2001 |

OTHER PUBLICATIONS

International Search Report for PCT International Application No. PCT/US2012/050717, dated Nov. 5, 2012, 3pgs.

*Primary Examiner* — Wade Miles
*Assistant Examiner* — Matthew P Saunders (57) ABSTRACT

Orthodontic appliances and related methods are provided, including a fast-dissolving and humidity-resistant coating, containing a colorant and a binder selected from a polyamide, cellulose derivative, or homopolymer/copolymer of poly(ethylene oxide). The coating can facilitate appliance identification and serve as a reference marking to assist the practitioner in appliance placement. Advantageously, the composition of these coatings allows the color marking to be rinsed off quickly, and yet the color of the coating does not bleed during storage even in high humidity environments. The fast-dissolving nature of these coatings also allows the coating to be deposited in concave and recessed areas of the appliance, such as the archwire slot and vertical slot, since these coatings can be removed prior to archwire installation.

20 Claims, 2 Drawing Sheets

(58) Field of Classification Search
USPC .............................................................. 433/8
See application file for complete search history.

(56) References Cited

U.S. PATENT DOCUMENTS

| | | | | | |
|---|---|---|---|---|---|
| 4,198,243 | A | * | 4/1980 | Tanaka | C09D 5/00 106/31.03 |
| 4,952,141 | A | * | 8/1990 | Wool | A61C 7/14 433/24 |
| 4,978,007 | A | | 12/1990 | Jacobs | |
| 5,040,554 | A | | 8/1991 | Rosenberger | |
| 5,074,783 | A | * | 12/1991 | Reher | A61C 7/12 433/24 |
| 5,203,804 | A | * | 4/1993 | Nikutowski | A61C 7/20 433/17 |
| 5,348,154 | A | | 9/1994 | Jacobs | |
| 5,350,059 | A | | 9/1994 | Chester | |
| 5,429,229 | A | | 7/1995 | Chester | |
| 5,674,067 | A | * | 10/1997 | Masel | A61C 7/303 433/18 |
| 5,674,513 | A | | 10/1997 | Snyder, Jr. et al. | |
| 5,692,896 | A | * | 12/1997 | Pospisil | A61C 7/14 206/369 |
| 5,716,208 | A | * | 2/1998 | Forman | A61C 7/14 433/24 |
| 5,762,192 | A | | 6/1998 | Jacobs | |
| 5,803,728 | A | * | 9/1998 | Orikasa | A61B 90/94 433/8 |
| 7,094,052 | B2 | | 8/2006 | Abels | |
| 2002/0114847 | A1 | * | 8/2002 | Peshoff | A61K 31/43 424/642 |
| 2005/0106112 | A1 | * | 5/2005 | Boyd | A61K 8/042 424/49 |
| 2005/0244776 | A1 | * | 11/2005 | Abels | A61C 7/146 433/10 |
| 2006/0210942 | A1 | | 9/2006 | Pace | |
| 2006/0216537 | A1 | * | 9/2006 | Natsui | D21H 19/12 428/537.5 |
| 2008/0262154 | A1 | * | 10/2008 | Behrens | C08F 2/18 524/801 |

* cited by examiner

ORTHODONTIC APPLIANCES WITH DISSOLVABLE COATINGS

CROSS REFERENCE TO RELATED APPLICATIONS

This application is a national stage filing under 35 U.S.C. 371 of PCT/US2012/050717, filed Aug. 14, 2012, which claims priority to US Provisional Application No. 61/526,939, filed Aug. 24, 2011, the disclosures of which are incorporated by reference in their entirety herein.

FIELD OF THE INVENTION

Provided are appliances and methods for use in orthodontic treatment. More particularly, provided are orthodontic appliances for attachment to tooth surfaces, and methods related thereof.

BACKGROUND

Orthodontics is a specialized area of dentistry in which therapeutic forces are applied to move maloccluded teeth to proper positions. The practice of orthodontics is supervised by a trained practitioner (e.g. orthodontist), who uses one or more orthodontic appliances to impart corrective forces directly to the teeth or stimulate or re-direct functional forces in the mouth to move teeth. Orthodontic treatment can provide a number of beneficial outcomes, including improved bite function, better hygiene and ease-of-cleaning, and enhanced facial aesthetics.

Fixed appliance therapy is one common type of treatment that involves attaching tiny slotted appliances called brackets to the teeth and coupling (or ligating) a resilient arch-shaped wire to the bracket slots. Upon installation, the wire shape is initially deflected to assume the crooked shape of the patient's dentition. Over time, however, the wire applies gentle corrective forces to the teeth as it returns to its original shape, thereby stimulating tooth movement toward desired finish positions. This process is generally repeated with progressively larger wires, with occasional adjustments to the wire made as needed, until the teeth positions are satisfactory to the practitioner.

One of the primary challenges with fixed appliance therapy is its reliance on accurate appliance placement on the tooth surface to move the teeth to desired finish positions. For example, if a particular bracket is located one millimeter too high on a certain tooth, then the wire would translate that tooth downward such that its final position is one millimeter too low. In this sense, these orthodontic appliances serve as precision handles to move teeth, and must be bonded to their respective teeth with great attention to appliance position on each tooth.

SUMMARY

With the advent of aesthetic orthodontic appliances that blend in with the color of the underlying tooth, it can be difficult for a practitioner to visualize and position these appliances on a patient's teeth with great accuracy. Some manufacturers place brightly-colored detachable guides in the archwire slots of the orthodontic appliances. These detachable guides can be color-coded to identify the appliance type and assist in aligning the appliance. While these guides provide adequate contrast against the tooth, they are inconvenient because an extra step is required by the practitioner to remove each of the guides after bonding the appliance to the tooth.

Other manufacturers put a common water soluble ink, dye, or other colorant on a facial surface of the bracket. This ink marking is present during bonding but subsequently dissolves in the patient's mouth, thereby preserving the aesthetics of the appliance. However, these too have their shortcomings First, some tend to "bleed" excessively in humid environments, rendering them unusable in certain climates. Second, those colorants that are able to survive humid environments do not dissolve sufficiently quickly to provide an aesthetic appearance when the patient leaves the chair.

Described herein are orthodontic articles and related methods that use a fast-dissolving and humidity-resistant coating derived from a binder selected from a polyamide, cellulose derivative, or homopolymer/copolymer of poly (ethylene oxide). This coating can serve as a marking to facilitate appliance identification and a reference marking to assist the practitioner in appliance placement. Advantageously, these coatings have a composition that allows the color marking to be rinsed off quickly, and yet the color of the coating does not bleed during storage even in high humidity environments. The fast-dissolving nature of these coatings also allows the coating to be deposited in concave and partially enclosed areas of the appliance, such as the archwire slot and vertical slot to easily visualize bracket position. Further, these coatings can adhere very well to the metal and ceramic appliance surfaces such that the coating does not inadvertently come off in shipment or use. Finally, the provided coating compositions can be sufficiently viscous to provide easy and accurate placement of the color indicia during manufacturing the appliance.

In one aspect, an orthodontic appliance is provided. The appliance comprises: a base; a body extending outwardly from the base, the body having an elongated archwire slot extending in a generally mesial-distal direction; a fast-dissolving and humidity-resistant coating extending over at least a portion of the body, the coating comprising: a colorant; and a binder selected from a polyamide, cellulose derivative, or homopolymer/copolymer of poly(ethylene oxide).

In another aspect, a method of providing a fast dissolving and humidity-resistant marking on an orthodontic appliance having an elongated archwire slot extending in a generally mesial-distal direction thereon is provided, the method comprising: compounding a water-insoluble pigment or water-soluble dye, a binder selected from a polyamide, cellulose derivative, or homopolymer/copolymer of poly(ethylene oxide), and a volatile solvent to form a dispersion or solution; applying the dispersion or solution on a surface of the orthodontic appliance; and evaporating the volatile solvent.

DEFINITIONS

As used herein:

"Mesial" means in a direction toward the center along a patient's curved dental arch.

"Distal" means in a direction away from the center along a patient's curved dental arch.

"Occlusal" means in a direction toward the outer tips of the patient's teeth.

"Gingival" means in a direction toward the patient's gums or gingiva.

"Facial" means in a direction toward the patient's lips or cheeks.

"Lingual" means in a direction toward the patient's tongue.

DETAILED DESCRIPTION

Figure 1:
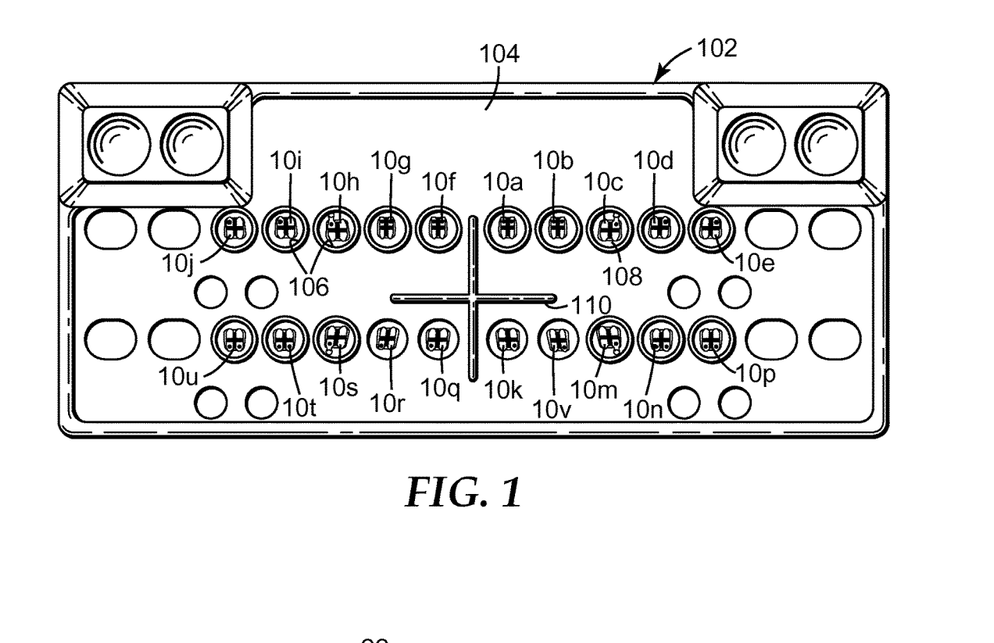
FIG. 1 is a plan view of a setup tray containing a number of orthodontic appliances according to one embodiment.

An orthodontic kit according to one exemplary embodiment is shown in FIG. 1 and designated by the numeral 100. The kit 100 comprises a patient setup tray 102 of a type commonly used in orthodontic offices. The tray 102 has a substrate 104 with a number of receptacles 106 arranged in a pattern that corresponds to respective teeth in the patient's oral cavity. Optionally and as shown, an adhesive coated film 108 extends along the bottom of the substrate 104, and can be exposed in areas beneath the receptacles 106 to releasably hold orthodontic brackets in place as the desired brackets are selected and brought to the patient.

Orthodontic brackets are arranged in the receptacles 106 of the tray 102. Each bracket has a brightly colored and dissolvable coating disposed in its archwire slot, vertical slot, and one or both of its gingival tiewings. In exemplary embodiments, the coatings disposed in the archwire slots and vertical slots are uniform in color, while the coatings on the tiewings have colors and configurations that vary based on bracket type (as will be described in more detail below). A raised cross-shaped indicia 110 formed in the substrate 104 provides a reference point in the setup tray which represents the midpoint of the patient's upper and lower dental arch.

Referring again to FIG. 1, the horizontal row of seven receptacles 106 on the upper right-hand side of the center of the indicia 110 corresponds to the row of teeth on the left-hand side of the patient's upper arch. The row of receptacles 106 to the upper left-hand side of the center of the indicia 110 corresponds to the row of teeth on the right-hand side of the patient's upper dental arch. Similarly, the two rows of receptacles 106 located to the lower right-hand side of the center of the indicia 110 and the lower left-hand side of the center of the indicia 110 correspond to teeth on the left-hand side and right-hand side of the patient's lower arch respectively.

Each of the brackets designated 10a-10e is adapted for use with a corresponding tooth on the left-hand side of the patient's upper arch. The bracket 10a is for use with an upper left central incisor tooth, 10b for an upper left incisor lateral tooth, 10c for an upper left cuspid tooth, 10d for an upper left first bicuspid tooth and 10e for an upper left second bicuspid tooth. The brackets 10f-10j are intended to use with teeth on the patient's upper right dental arch quadrant. Bracket 10f is adapted for use with an upper right central incisor tooth, 10g for an upper right first lateral tooth. 10k for an upper right cuspid tooth, 10i for an upper right first bicuspid tooth and 10j for an upper right second bicuspid tooth.

The brackets 10k, 10v, 10m, 10n, and 10p are configured for use with respective teeth in the patient's lower left dental arch quadrant. The bracket 10k is intended for use with the lower left central incisor tooth, 10v for the lower left lateral incisor tooth, 10m for the lower left cuspid tooth, 10n for the lower left first bicuspid tooth and 10p for the lower left second bicuspid tooth. The brackets 10q-10u are adapted for use with corresponding teeth in the patient's lower right dental arch quadrant. Bracket 10q is for a lower right central incisor tooth. 10r for a lower right lateral incisor tooth, 10s for a lower right cuspid tooth, 10t for a lower right first bicuspid tooth and 10u for a lower right second bicuspid tooth.

In one preferred embodiment, brackets 10a and 10f have a coating with a blue color, brackets 10b and 10g have a coating with a red color, brackets 10c and 10h have a coating with a green color, brackets 10d, 10e, 10i and 10j have a coating with a yellow color, brackets 10k, 10v, 10q and 10r have a coating with a pink color, brackets 10m and 10s have a coating with a purple color, brackets 10n and 10t have a coating with a light blue color and brackets 10p and 10u have a coating with a light grey color. In some embodiments, eight different colors for the coating are used when twenty brackets, or five brackets in each of the arch quadrants, are employed. The upper bicuspid brackets (i.e., brackets 10d, 10e, 10i, and 10j) may have a coating of the same color, and the lower anterior brackets (i.e., lower central and lateral incisor brackets 10k, 10v, 10q and 10r) may have a coating of the same color (or be provided without a coating) since the brackets within each group are essentially the same.

Alternatively, the brackets could be identified by means other than color. For example, they could be identified by an applied indicia. The indicia can be numeric, alphabetic, alphanumeric, geometric, symbolic, or any other distinguishing marking. For example, it is possible to divide the teeth into the four quadrants and start at the front and number 1-8 to represent the eight teeth in each arch. Each quadrant would have a number and then the tooth number after it. In addition, it may be desirable to draw an "L" shaped angle around the number and point the "arms" of the "L" in the direction of the quadrant. For example, an "L" with the number "3" written in it would be the upper left canine). These indicia can be of any suitable color and can be applied by any suitable means such as a stamp or ink jet method.

Figure 2:
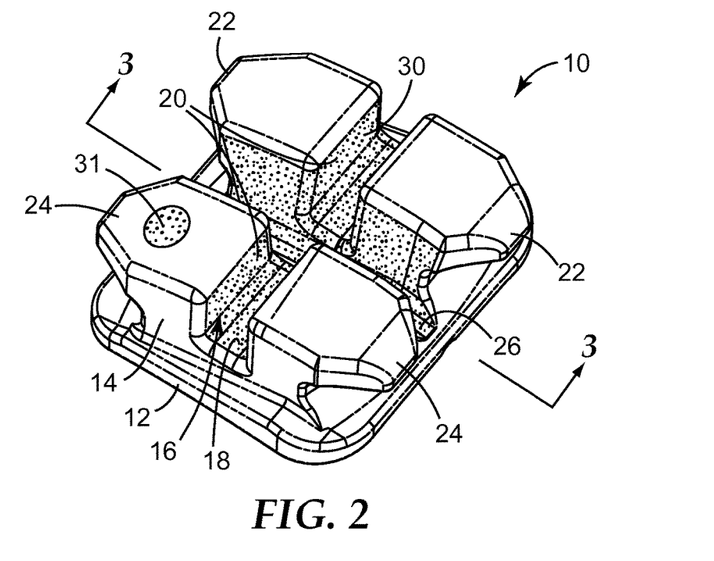
FIG. 2 is a perspective view of an orthodontic appliance taken from FIG. 1, showing its mesial, occlusal and facial sides.
Figure 3:
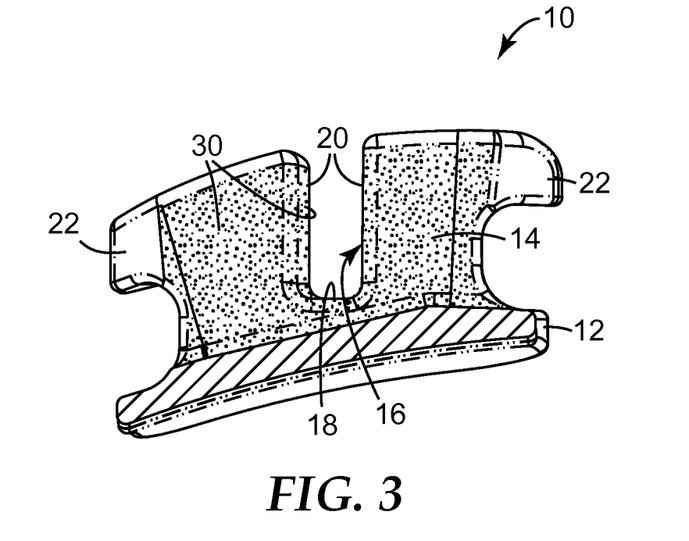
FIG. 3 is a cross-sectional view of section 3-3 taken of the appliance shown in FIG. 2, showing cross-sectional components of the bracket.
Figure 4:
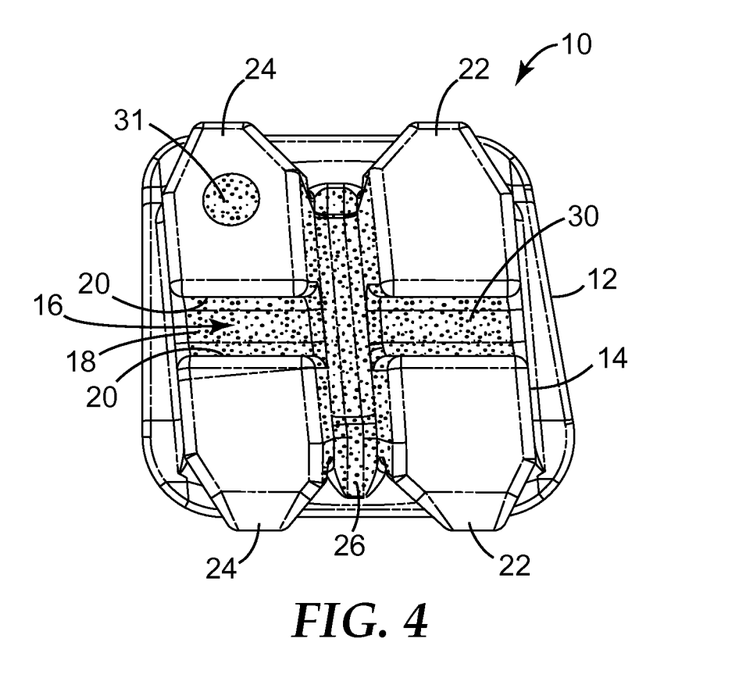
FIG. 4 is a front elevational view of the orthodontic appliance in FIGS. 2-3 as viewed when looking toward its facial side.

FIGS. 2-4 show perspective, cross-sectional, and facial views of an exemplary orthodontic bracket 10 in the kit 100. As shown, the bracket 10 includes a base 12 and a body 14 extending outwardly from the base 12 in a generally facial direction. Preferably, the base 12 has a lingual-facing surface with a compound curvature generally conforming to the convex contour of a corresponding tooth surface. An elongated archwire slot 16 extends in a generally mesial-distal direction across the facial surface of the body 14 for accommodating a suitable archwire during the course of treatment. As shown, the archwire slot 16 has a bottom wall 18 and opposing sidewalls 20.

To provide anchor points for ligating the archwire to the body 14, a pair of mesial tiewings 22 and a pair of distal tiewings 24 extend from respective mesial and distal sides of the body 14. Each pair of tiewings 22, 24 protrudes in occlusal and gingival directions. Extending across the body 14 in a generally occlusal-gingival direction is a vertical slot 26, which resides between the tiewings 22, 24 and generally divides the bracket 10 into mesial and distal halves.

The bracket 10 can be made from any of a variety of different materials. These materials include, for example, ceramic materials such as monocrystalline or polycrystalline alumina, metal materials such as stainless steel, and polymeric materials such as glass-filled polycarbonate. Preferably, the bracket 10 is made from a translucent material such that the bracket appears to have the color of the underlying tooth surface.

As further shown in some views of FIGS. 2-4, a coating 30 is selectively disposed in the archwire slot 16 and the vertical slot 26 of the bracket 10. Preferably, in one embodiment, the coating 30 has a vibrant color contrasting with that of the bracket 10. Advantageously, the coating 30 provides sufficient contrast allowing a practitioner to easily visualize the position and orientation of an otherwise translucent bracket 10 against the tooth.

Optionally, and as shown in FIGS. 2 and 4, the coating 30 is also present as a separate indicia 31 (here, an identification "dot") on the facial surface of the distal-gingival tiewing 24. As described with respect to the brackets in FIG. 1, the indicia 31 assists the practitioner in determining at a glance which tooth corresponds to a given bracket. The position of the indicia 31 can also assist in preventing brackets from opposing quadrants from being accidently reversed in the setup tray 102.

The coating 30 includes a colorant and a water-soluble polymeric binder. In some embodiments, the coating 30 is prepared using a solvent casting process. In this process, a composition is first prepared containing the colorant, water-soluble polymeric binder, and suitable volatile solvent. After compounding the colorant, binder, and solvent to form a suitable dispersion, the dispersion can be disposed on one or more surfaces of the orthodontic appliance. The dispersion can then be dried, either under heat or under ambient conditions, to evaporate the volatile solvent and form the coating 30.

The colorant can be a dye or a pigment. As used herein, a dye is a colorant that is soluble in deionized water and a pigment is essentially insoluble in deionized water. When added to deionized water at 0.1%, a dye will generally form a uniform color throughout, whereas a pigment will form a separate phase and leave the water clear without color or with very little coloration relative to a dye (e.g. the lake ionic complex of a dye is far less soluble than the dye but may have trace levels of uncomplexed dye).

Preferably the colorant is a water-insoluble pigment. Pigments avoid potential problems with staining the bracket substrate and/or staining the tissue of the patient (e.g. gums, teeth, tongue, and buccal tissue). The pigment is preferably a pharmaceutically acceptable pigment and may be inorganic such as titanium dioxide and iron oxides, or organic such as lakes of FD&C or D&C dyes such as aluminum lakes and combinations thereof.

In certain embodiments, a dye may be preferred. For example, since the provided dyes are water soluble there is no phase separation and settling can be avoided. Both of these aspects can facilitate manufacturing. Preferred dyes are FD&C dyes or D&C dyes which are pharmaceutically acceptable to the US Food and Drug Administration (FDA) for oral use. Cationic, anionic or nonionic dyes may be used. Dyes could be chosen that will not adversely stain the bracket substrate. For example, for many anionically surface-charged ceramics, anionic dyes may be preferred.

The water-soluble polymer binder is preferably a food-grade, pharmaceutically acceptable polymer. Preferred polymers can be found in the "Inactive Ingredient List for Approved Drug Products," available on the U.S. FDA website. In one preferred embodiment, the polymer binder contains a water-soluble vinyl polymer comprising amide groups (polyamide). The polyamide may be a substantial component of the binder, where the polyamide has a weight composition that is greater than any other component of the binder. In some embodiments, however, the binder consists essentially of polyamide.

The polyamide may be nonionic, cationic, anionic or zwitterionic. The polyamide is preferably a polylactam. The polylactam is preferably based on n-vinyl pyrrolidone (NVP) or n-vinyl caprolactam. Other polyamides formed from secondary amines having no N—H in the amide bond may also be suitable such as N, N dialkylacrylamides such as dimethylacrylamide. These polyamides comprise monomers having the following functional group:

(R1)(R2)-N—C(O)—R3, where R1, R2 and R3 each are independently aliphatic or aromatic hydrocarbon moieties optionally substituted with one or more of N, O, and S with the understanding that R1, R2 or both may form a ring with R3 such as a pyrrolidone ring. At least one of R1, R2, and R3 comprises a polymerizable group such as an ethylenically unsaturated group.

In some embodiments, the polylactam is an n-vinyl pyrrolidone copolymer containing one or more other monomers such as vinyl acetate, alkenes such as GANEX brand resins (International Specialty Products (ISP) in Wayne, N.J.), cationic monomers such as dimethylaminoethylmethacrylate in GAFQUAT brand resins (ISP), diallyldimethylammonium chloride, alkyl acrylates, styrene, methoxypolyethyleneglycol (MPEG) acrylates, acrylic acid, methacrylic acid, and hydroxyethylmethacrylate. The copolymer (or terpolymer) containing at least one vinyl pyrrolidone monomer and/or at least one vinyl caprolactam monomer can be selected from the group consisting of vinyl pyrrolidone/vinyl caprolactam/dimethylaminoethylmethacrylate (DMAEMA) (available from ISP as ADVANTAGE brand S, ADVANTAGE brand HC-37, and ADVANTAGE brand LC-E), vinyl pyrrolidone/vinyl caprolactam/dimethylaminopropylmethylacrylamide (DMAEMA) acrylate (AQUAFLEX brand SF-40, from ISP), vinyl pyrrolidone/vinyl caprolactam/dimethylaminopropylmethylacrylamide acrylate/methacryloylaminopropyl lauryldimethylammoniumchloride (AQUASTYLE brand 300, from ISP) and vinyl pyrrolidone/vinyl caprolactam (LUVITEC brand 55K, 65W, from BASF SE in Ludwigshafen, Germany)

Also suitable in some embodiments are polymers based on amides from primary amines These amides still possess a N—H group that may improve hydrogen bonding and adhesion to certain substrates. These polyamides comprise monomers having the group shown above where R2 is hydrogen (H):

(R1)H—N—C(O)—R3, where R1 and R3 are each independently aliphatic or aromatic hydrocarbon moieties optionally substituted with one or more of N, O, and S with the understanding that R1 may form a ring with R3 such as a pyrrolidone ring. Again, at least one of R1 and R3 comprises a polymerizable group, such as an ethylenically unsaturated group.

Examples include polymers based on C1-C18 straight or branched chain alkyl acrylamides such as methacrylamide, isopropylacrylamide, octylacrylamide, octadecylacrylamide, and the like. As an alternative to the above, the polyamide could have an acrylamide formula where R1 is replaced by a hydrogen group:

Generally, suitable polyamides may be nonionic, cationic, or anionic and based on monomers such as acrylamide, acrylamidopropyl trimethyl ammonium chloride (APTAC), methacrylamidopropyl trimethyl ammonium chloride (MAPTAC), and methyl quaternized vinyl imidazole, acrylic acid, methacrylic acid and the like.

In some embodiments, the polylactam has a weight average molecular weight of at least 15,000 daltons (i.e. grams per mole), at least 30,000 daltons, or at least 45,000 daltons. In some embodiments, the polylactam has a weight average molecular weight of up to about 1,000,000 daltons, up to about 500,000 daltons, up to about 250,000 daltons, up to about 120,000 daltons, up to about 90,000 daltons, or up to about 70,000 daltons.

Alternatively or in combination, the binder can include a water-soluble cellulose derivative such as carboxymethylcellulose, hydroxypropylmethylcellulose, hydroxyethylcellulose. Alternatively or in combination, the binder could also include poly(ethylene oxide) as well as water soluble copolymers of ethylene oxide and propylene oxide such as poloxamers having at least 50 mole percent ethylene oxide. Alternatively or in combination, the binder can include homo- and copolymers of 2-ethyloxazoline and/or homo- and copolymers of acrylamide and dimethyl or diethylacrylamide.

Optionally a plasticizer may be included in the coating composition, for example to keep the polymer soft and adherent to the bracket surface. The plasticizer is preferably compatible with the polymer such that dried solutions of polymer and plasticizer form suitably homogenous single phase films. As used herein a "plasticizer" is a compound when suitably uniformly blended into the binder increases the flexibility of the binder and typically reduces the glass transition temperature. Preferred plasticizers include polyhydric alcohols such as propylene glycol, glycerol, butane diol, poly(ethylene glycol) having a molecular weight of at least 200 and preferably at least 400 and preferably less than 8000 and more preferably less than 2000 daltons, glycereth-7, sorbitol, mannitol, and xylitol.

In one preferred embodiment, the coating is prepared from a solvent-based ink formulation. Preferably, the solvent is capable of fully dissolving the polymer binder. Suitable solvents can be selected from any of a number of solvents having low heat of vaporization for rapid evaporation. Preferred solvents include ethyl alcohol and isopropyl alcohol.

Preferably, the ink formulation facilitates a controllable and uniform coating. The ink composition preferably remains physically and chemically stable for a reasonable shelf life without undesirable caking or particle settling. The most preferred compositions show no macroscopic phase separation after removing from mixing for 60 minutes. In many embodiments that use pigments there is a minimum dispersion/solution viscosity. Preferably, the viscosity of the ink is sufficiently thin to flow and coat the bracket slots while also sufficiently thick to avoid overflowing onto the bracket sides.

The thickness of the coating should be sufficiently high that it can provide a vibrant color and contrast on the underlying substrate, allowing it to be easily distinguished by the naked eye. However, the coating thickness should also be sufficiently low it can dissolve quickly in water. Moreover, the composition should also be relatively thin so it does not unduly protrude above the surface of the substrate, which could adversely affect coating durability. In some embodiments, the normalized coating weight ranges between about 2 and 10 milligrams per square centimeter, or approximately 20-100 micrometers in thickness. Within this range, the dissolution percent is not significantly affected by the coating thickness since the dissolution percent is normalized by the coating weight. At significantly higher thicknesses, the dissolution percent can be affected. It was found that below about 1 milligram per square centimeter, the color appears light and does not provide a sharp contrast against ceramic brackets.

Thermoplastic coating compositions also are possible. For example, certain polyamides when plasticized may be thermally processed similar to a hot melt adhesive. If a polyamide is used as a binder, the polyamide may be mixed with a thermoplastic water soluble polymer such as a plasticized modified cellulose (e.g. hydroxypropylmethyl-cellulose), polyethylene oxide, and the like. These thermoplastic compositions are selected to adhere to the substrate and later remove rapidly by contact with water.

After the coating 30 has been duly disposed on the bracket body 14 and carrier solvent removed, the bracket 10 is ready for use. At this point, the bracket 10 can be packaged as part of a set of brackets as shown by the one-case kit of FIG. 1. Alternatively, but not shown here, the bracket can be coated with a light-curable orthodontic adhesive and stored in a container to facilitate organization and dispensing, as described for example, in U.S. Pat. No. 4,978,007 (Jacobs et al.), U.S. Pat. No. 5,348,154 (Jacobs et al.), U.S. Pat. No. 5,762,192 (Jacobs et al.), U.S. Pat. No. 5,350,059 (Chester et al.) and U.S. Pat. No. 5,429,229 (Chester et al.).

The attachment of the bracket 10 to a respective tooth of the patient can be done using any of a number of direct or indirect bonding methods known in the art. After all of the brackets have been bonded, and prior to the placement of an archwire, the practitioner can have the patient vigorously rinse the oral cavity with water to remove the coating 30.

Coating compositions based on a binder selected from a polyamide, cellulose derivative, or homopolymer/copolymer of poly(ethylene oxide) have significant and unexpected advantages over conventional coating compositions. For example, these coatings can be fast dissolving/dispersing, humidity resistant, and have excellent durable adhesion to the substrate. As used herein, the term "dissolve" generically refers to the removal of the colorant (including both dyes and pigments) by rinsing with a suitable solvent such as, for example, de-ionized water. It is preferable that these coatings dissolve in the usual timeframe between the bonding of brackets to the teeth and the placement of the archwires in the wire slots of the brackets. In some embodiments, this timeframe extends over at least 5 minutes, at least 7 minutes or at least 10 minutes.

Previously, the above features have not been achieved in the same composition. On one hand, coatings that dissolve easily also tend to run, smear, or "bleed," when subjected to high humidity environments. This "bleeding" behavior is unacceptable. On the other hand, coatings that withstand humid environments often dissolve slowly in water. In some cases, toothbrushing is required to facilitate removal of these coatings. This too is undesirable, because ink coatings detract from the aesthetics of the appliance and should be easily and conveniently removed. Surprisingly, the inventive coatings are substantially removed from around 2 minutes of rinsing with water, and yet display limited to essentially zero bleed even after storage in a 75% relative humidity environment. Furthermore, the preferred coatings described herein are adhered very well to the substrate and do not come off even when subjected to shake testing. This is important since it is undesirable for the coatings to dislodge during transport and storage of the orthodontic appliances.

In preferred embodiments, at least 60 percent, at least 75 percent, or at least 85 percent by weight of the coating dissolves when the appliance is subjected to the Dissolution Test (described in the Examples section below) and the coating displays no adverse sagging, bleeding, or flaking from the substrate after being subjected to a relative humidity of 75 percent at 40 degrees Celsius for 4 weeks.

The features of the above paragraph also give rise to other significant advantages. For example, the fast-dissolving nature of the coatings allows them to be disposed in recessed areas of the bracket, such as the archwire slot and vertical slot. Application of coatings in these enclosed areas can be particularly challenging, since any undissolved coating can interfere with slot dimensions as well as the sliding mechanics of the appliance. In conventional appliances, these areas often remain uncoated because toothbrush access is limited and archwire placement could interfere with the removal of any undissolved coating. In various embodiments described herein, however, the dissolution is sufficiently rapid that the coating can be fully removed before the archwire is placed. Finally, because of the fast-dissolving nature of the coating, tooth brushing is not required to remove the coating. Nevertheless, some practitioners may recommend brushing before archwire insertion to ensure removal of any coating in archwire slots and removal of other coating debris.

EXAMPLES

Objects and advantages of the disclosed embodiments are further illustrated by the following examples. The particular materials and amounts thereof recited in these examples, as well as other conditions and details, should not be construed to unduly limit this invention. Unless otherwise indicated, all parts and percentages are by weight and all molecular weights are weight average molecular weight.

As used herein:
"Blue" refers to FD&C Blue #1 Lake;
"Green" refers to FD&C Emerald Green Lake, a mixture of FD&C Blue #1 Lake and FD&C Yellow #5 Lake;
"Red" refers to FD&C Red #40 Lake;
"Blue Dye" refers to FD&C Blue #1;
"PVP" in the examples without molecular weight specified refers to polyvinyl pyrrolidone having a weight average molecular weight of 58,000 daltons, provided as Plasdone K-29/32 from International Specialty Products, Inc.;
"PVP (MW 34,000)" refers to polyvinyl pyrrolidone described as having a weight average molecular weight of 34,000 daltons, provided as Plasdone K-25 from International Specialty Products, Inc.;
"PVP (MW 10,000)" refers to polyvinyl pyrrolidone described as having a weight average molecular weight of 10,000 daltons, provided as Plasdone K-17 from International Specialty Products, Inc.,
"PVP (MW 360,000)" refers to PVP described as having a weight average molecular weight of 360,000 daltons, provided by Alfa Aesar (Ward Hill, Mass.);
"PVP/VA" refers to a copolymer of vinylpyrrolidone and vinyl acetate, provided as Plasdone S630 from International Specialty Products, Inc.;
"HPMC" refers to hydroxypropylmethylcellulose, provided as Methocel E3 Premium LV from Dow Chemical (Midland, Mich.);
"PEO" refers to poly(ethylene oxide), provided as Polyox WSR N10 from Dow Chemical;
"PEG 400" refers to poly(ethylene glycol), described as having a number average molecular weight of 400 daltons and provided from Sigma Aldrich (St. Louis, Mo.);
"PEG 600" refers to poly(ethylene glycol) described as having a number average molecular weight of 600 daltons and provided from Sigma Aldrich;
"PAA water" refers to polyacrylamide, 50% in water, described as having a weight average molecular weight of 10,000 daltons and provided from Sigma Aldrich;
"PAADDA water" refers to polyacrylamide-co-diallyldimethylammonium chloride, 10% in water, 55% acrylamide, provided from Sigma Aldrich; and
"VCL/VP/DMAEMA" refers to vinyl caprolactam/vinyl pyrrolidone/dimethylaminoethyl methacrylate terpolymer, provided as Advantage S by International Specialty Products, Inc.

Coatability Test

Alumina bracket slots were coated using a dispensing system, Portion-Aire Bench Top Dispenser PV-2000 from Glenmark Industries Inc. The ink formulation of interest was placed into a syringe and pressurized. Upon activation, the ink formulation flowed out of a needle tip for a pre-set period of time to coat the bracket slots. The pressure was set between 7 and 15 psi. Both the pressure and time could be adjusted to obtain a uniform coating on the slots and as the identification (ID) dot. The coated brackets were then dried at 50 degrees Celsius for 10 minutes unless otherwise noted. New ink formulations are compared to the inks based on those (controls) currently used for the ID dots of CLARITY brand ceramic brackets (3M Unitek in Monrovia, Calif.). Finally, the relative ease or difficulty of applying the ink formulation was recorded.

Dissolution Test

To measure the rate at which an appliance coating dissolves in water, the following steps were conducted:
1) Weigh 10-11 brackets to obtain the weight of coated brackets.
2) Place the brackets on the tacky surface of a bonding prep tray (3M Unitek, REF 709-029) and cut the tray to fit snugly inside a 150 milliliter beaker.
3) Place the beaker in a shaker bath containing water at 37° C. and a circular motion of 150 rpm.
4) At t=0, add 20 milliliters of distilled water to the beaker covering the brackets on the tray to start dissolution.
5) After 120 seconds, remove the brackets on the tray from water, dry the brackets in an oven heated to 100° C., and weigh the brackets.
6) Continue to completely dissolve any residual coatings by rinsing the brackets with water. For coatings that are hard to be rinsed off by water, additionally sonicate the brackets in water, 5% ammonium hydroxide aqueous solution or Alconox Powdered Precision Cleaner (1:100 in water) to completely remove the coatings. Dry brackets. Weigh the uncoated brackets.
7) The percentage of reference marks dissolved at 120 seconds is calculated as the weight of the coatings removed at 120 seconds (i.e. weight of brackets with coatings—weight of brackets with residual coatings after 120 seconds) as a percentage of total coating weight (i.e. weight of brackets with coatings—weight of brackets without coatings).
8) Each measurement reflects the average coating loss for at least 10 bracket specimens.

Humidity Test

The following steps were followed to measure the resistance of appliance coating to elevated levels of humidity:
1) Place brackets with facial side up in their own individual compartments inside a plastic box (current package for CLARITY brand brackets).
2) Store the box in a 40° C./75% relative humidity chamber. Expose brackets with the cover of the box in an open position.
3) Examine whether the colored coatings remain sharp and do not bleed upon absorbing moisture.

Shake Test

To measure the adhesion of a coating to the appliance, the following steps were conducted:
1) Place 16 or 32 test brackets in a 150 milliliter cup along with 1000 "dummy" brackets. Cap the cup.
2) Place the cup in a Shaker Mixer, TURBULA brand Type T2 C (Glen Mills, Inc. in Clifton, N.J.). Set the speed to 60 rpm and conduct the shake test for 200 seconds to complete 200 cycles.
3) Remove all brackets from the cup. Separate test brackets from dummy brackets. Examine whether the test brackets retain the colored identification dot coatings and slot coatings.

Examples 1-5

Different formulations using Red were examined in Examples 1-3. In this series, the amount of Red used was held constant at 1.5% and the amount of PVP varied from 50% to 30%. The amount of solvent, ethyl alcohol, was increased proportionally to the decrease in the amount of PVP, and ranged from 48.5% to 68.5%. Formulations using Blue were examined in Examples 4-5. In this series, the amount of Blue used was held constant at 3.0%. Again, the amount of PVP varied from 50% to 40% while the amount of ethyl alcohol was proportionally increased from 47% to 57%. Observations on coatability are provided in Table 1 below.

TABLE 1

Coatability Test Results with Red and Blue

| Example/Comparative | Composition | Coating result |
|---|---|---|
| 1 | 1.5% Red/50% PVP/48.5% ethyl alcohol | Difficult to coat |
| 2 | 1.5% Red/40% PVP/58.5% ethyl alcohol | Easy to coat without overflow |
| 3 | 1.5% Red/30% PVP/68.5% ethyl alcohol | Some overflow, flowed beyond slot to the side of bracket |
| 4 | 3.0% Blue/50% PVP/47% ethyl alcohol | Difficult to coat |
| 5 | 3.0% Blue/40% PVP/57% ethyl alcohol | Easy to coat without overflow |

Examples 6-11

Formulations using Green were examined in Examples 6-11. In this series, the amount of Green used was held constant at 2.0%. In Example 6, the amount of PVP was 40% and the amount of ethyl alcohol was 58%. In Examples 7-9, the amount of PVP (MW 360,000) varied from 30% to 15% while the amount of ethyl alcohol was proportionally increased from 68% to 83%. In Example 10, PVP/VA was examined as a binder material. In Example 11, a 50:50 blend of PVP/VA and PVP was examined as a binder.

TABLE 2

Coatability Test Results with Green

| Example/Comparative | Composition | Coating result |
|---|---|---|
| 6 | 2.0% Green/40% PVP/58% ethyl alcohol | Easy to coat without overflow, good viscosity |
| 7 | 2.0% Green/30% PVP (MW 360,000)/68% ethyl alcohol | Difficult to coat, too viscous/stringy |
| 8 | 2.0% Green/20% PVP (MW 360,000)/78% ethyl alcohol | Somewhat difficult to coat, slightly viscous/stringy |
| 9 | 2.0% Green/15% PVP (MW 360,000)/83% ethyl alcohol | Difficult to control overflow, runny |
| 10 | 2.0% Green/40% PVP/VA/58% ethyl alcohol | Easy to coat without overflow, good viscosity |
| 11 | 2.0% Green/20% PVP/20% PVP/VA/58% ethyl alcohol | Easy to coat without overflow, good viscosity |

Examples 12-35

Ink formulations using Blue were examined in Examples 12-35. The amount of Blue used was held constant at 3.0% except for Example 23 where 0.5% Blue dye was used. In Example 12, PVP/VA was examined as a binder material. In Examples 13-14, PVP was used as a binder material with isopropyl alcohol or ethyl alcohol/water as solvent. Example 15 was dried at room temperature. Example 16 used PVP (MW 34,000) as binder material. Examples 17-20 used PVP (MW 10,000) as binder at quantities ranging from 40-60% and solvent levels ranging from 57% to 37%. Example 21 used PVP/VA as binder and isopropyl alcohol as solvent. Example 22 used an asymmetric blend of PVP (MW 10,000) and PVP/VA and ethyl alcohol as solvent. Example 23 used 0.5% Blue Dye as colorant. Examples 24-28 used 40% PVP as binder but used varying amounts of different plasticizers, including propylene glycol, glycerol, and PEG. Examples 29 and 30 used HPMC and PEO as binder materials, respectively. Example 31 used PAA as binder material and water as solvent. Example 32 used PAADDA as binder material with water/ethyl alcohol as solvent. Example 33 used PAADDA as binder material and water as solvent. Examples 34 and 35 used VCL/VP/DMAEMA as binder material with ethyl alcohol and water as solvent, respectively.

For each Example or Comparative, the ink formulation was examined using the Coatability Test (see above) and visual observations recorded. The results are shown in Table 3 below.

TABLE 3

Coatability Test Results with Blue

| Example/Comparative | Ink formulation | Coating result |
|---|---|---|
| 12 | 3.0% Blue/40% PVP/VA/57% ethyl alcohol | Easy to coat without overflow, good viscosity |
| 13 | 3.0% Blue/40% PVP/57% isopropyl alcohol | Easy to coat without overflow, good viscosity |

TABLE 3-continued

Coatability Test Results with Blue

| Example/Comparative | Ink formulation | Coating result |
|---|---|---|
| 14 | 3.0% Blue/40% PVP/5% water/52% ethyl alcohol | Easy to coat without overflow, good viscosity |
| 15 | Same as Example 5 Blue PVP but dried at RT | Easy to coat without overflow, good viscosity |
| 16 | 3.0% Blue/40% PVP (MW 34,000)/57% ethyl alcohol | Easy to coat without overflow, good viscosity |
| 17 | 3.0% Blue/40% PVP (MW 10,000)/57% ethyl alcohol | Difficult to control overflow, runny |
| 18 | 3.0% Blue/50% PVP (MW 10,000)/47% ethyl alcohol | Easy to coat without overflow, good viscosity |
| 19 | 3.0% Blue/55% PVP (MW 10,000)/42% ethyl alcohol | Easy to coat without overflow, good viscosity |
| 20 | 3.0% Blue/60% PVP (MW 10,000)/37% ethyl alcohol | Difficult to coat, stringy |
| 21 | 3.0% Blue/40% PVP/VA/57% isopropyl alcohol | Easy to coat without overflow, good viscosity |
| 22 | 3.0% Blue/30% PVP (MW 10,000)/20% PVP/VA/57% ethyl alcohol | Easy to coat without overflow, good viscosity |
| 23 | 0.5% Blue Dye/40% PVP/59.5% ethyl alcohol | Easy to coat without overflow, good viscosity |
| 24 | 3.0% Blue/40% PVP/4% propylene glycol/53% ethyl alcohol | Easy to coat without overflow, good viscosity |
| 25 | 3.0% Blue/40% PVP/2% propylene glycol/55% ethyl alcohol | Easy to coat without overflow, good viscosity |
| 26 | 3.0% Blue/40% PVP/2% glycerol/55% ethyl alcohol | Easy to coat without overflow, good viscosity |
| 27 | 3.0% Blue/40% PVP/2% PEG 400/55% ethyl alcohol | Easy to coat without overflow, good viscosity |
| 28 | 3.0% Blue/40% PVP/2% PEG 600/55% ethyl alcohol | Easy to coat without overflow, good viscosity |
| 29 | 3.0% Blue/20% HPMC/25% water/52% ethyl alcohol | Easy to coat without overflow, good viscosity |
| 30 | 3.0% Blue/15% PEO/25% water/57% ethyl alcohol | Easy to coat without overflow, good viscosity |
| 31 | 3.0% Blue/97% PAA water | Easy to coat without overflow, good viscosity |
| 32 | 3.0% Blue/66% PAADDA water/32% ethyl alcohol | Easy to coat without overflow, good viscosity |
| 33 | 3.0% Blue/50% PAADDA water/47% water | Easy to coat without overflow, good viscosity |
| 34 | 3.0% Blue/29% VCL/VP/DMAEMA/68% ethyl alcohol | Easy to coat without overflow, good viscosity |
| 35 | 3.0% Blue/22% VCL/VP/DMAEMA/75% water, pH adjusted to 7 using acetic acid | Easy to coat without overflow, good viscosity |

Examples 36-45 and Comparatives CE-1, CE-2, and CE-3

In this series, various bracket coatings were subjected to the Dissolution Test (see above). Comparative CE-1 was provided by alumina brackets coated with blue ink used for commercially available CLARITY brand brackets having a blue identification dot. Comparatives CE-2 and CE-3 were provided by a RADIANCE brand bracket (American Orthodontics in Sheboygan, Wis.) and ICE brand bracket (Ormco Corporation in Orange, Calif.), respectively. The polymer binder of the RADIANCE brand bracket is believed to be based on poly(vinyl alcohol—vinyl acetate), or polyvinyl acetate and polyglycol. The polymer binder of the ICE brand bracket is believed to be based on polyglycol and/or poly vinyl alcohol. Neither of the binders used in these comparative examples is believed to contain a polyamide, cellulose derivative, or homopolymer/copolymer of poly(ethylene oxide). Examples 36-45 were prepared using the ink formulations of Examples 5, 12, 23, 29, 30, 31, 32, 33, 34 and 35, respectively. The results of the Dissolution Test are shown in Table 4 below. Colored coatings in Table 4 were either totally removed or mostly removed to be slightly visible after Dissolution Test except for CE-1 and CE-2.

TABLE 4

Dissolution Test Results

| Example/Comparative | Bracket | Average coating amount dissolved at 2 minutes (%) |
|---|---|---|
| CE-1 | Alumina bracket coated with the blue ink used for CLARITY brand bracket with blue dot | 33* |
| 36 | Alumina bracket coated with Blue PVP (from Example 5) | 90 |
| 37 | Alumina bracket coated with Blue PVP/VA (from Example 12) | 90 |
| 38 | Alumina bracket coated with Blue Dye PVP (from Example 23) | 100 |
| 39 | Alumina bracket coated with Blue HPMC (from Example 29) | 74 |
| 40 | Alumina bracket coated with Blue PEO (from Example 30) | 82 |
| 41 | Alumina bracket coated with Blue PAA (from Example 31) | 91 |
| 42 | Alumina bracket coated with Blue PAADDA (from Example 32) | 77 |
| 43 | Alumina bracket coated with Blue PAADDA (from Example 33) | 90 |
| 44 | Alumina bracket coated with Blue VCL/VP/DMAEMA (from Example 34) | 84 |
| 45 | Alumina bracket coated with Blue VCL/VP/DMAEMA (from Example 35) | 80 |
| CE-2 | RADIANCE brand bracket | 45** |
| CE-3 | ICE brand bracket | 100 |

*Dot coating still visible after 2 minutes of dissolution
**Slot coatings still visible after 2 minutes of dissolution

Examples 46-54 and Comparatives CE-4, CE-5 and CE-6

This series examines the effect of high humidity on coated brackets. Examples 46-54 used coatings based on the ink formulations of Examples 5, 12, 23, 29, 30, 31, 32, 33 and 34, respectively, while Comparatives CE-4, CE-5 and CE-6 used an ICE brand bracket, a RADIANCE brand bracket and a CLARITY brand bracket, respectively. When tested in the humidity chamber, CE-4 began to smear and flow. This "bleeding" behavior is unacceptable. The results of the Humidity Test are provided in Table 5 below.

TABLE 5

Humidity Test Results

| Example/Comparative | Bracket | Appearance over time at 40° C./75% RH |
|---|---|---|
| 46 | Alumina bracket coated with Blue PVP (from Example 5) | Good. No signs of bleeding after 4 weeks. |
| 47 | Alumina bracket coated with Blue PVP/VA (from Example 12) | Good. No signs of bleeding after 4 weeks. |
| 48 | Alumina bracket coated with Blue Dye PVP (from Example 23) | Good. No signs of bleeding after 4 weeks. |
| 49 | Alumina bracket coated with Blue HPMC (from Example 29) | Good. No signs of bleeding after 4 weeks. |
| 50 | Alumina bracket coated with Blue PEO (from Example 30) | Fair. Slight bleeding of dot coatings by day 3. Not much worse at 4 weeks. Bleeding of slot coating barely noticeable. |
| 51 | Alumina bracket coated with Blue PAA (from Example 31) | Good. No signs of bleeding after 4 weeks. |
| 52 | Alumina bracket coated with Blue PAADDA (from Example 32) | Fair. Slight bleeding of dot coatings by day 5. Not much worse at 4 weeks. Bleeding of slot coating barely noticeable. |
| 53 | Alumina bracket coated with Blue PAADDA (from Example 33) | Good. No signs of bleeding after 4 weeks. |
| 54 | Alumina bracket coated with Blue VCL/VP/DMAEMA (from Example 34) | Good. No signs of bleeding after 4 weeks. |
| CE-4 | ICE brand bracket | Considerable bleeding. After 2.5 hours, dot coatings and facial tiewing coatings partially dissolved/flowed. |
| CE-5 | RADIANCE brand bracket | Good. No signs of bleeding after 4 weeks. |
| CE-6 | CLARITY brand bracket | Good. No signs of bleeding after 4 weeks. |

Examples 55-60 and Comparatives CE-7 and CE-8

This series examines the effect of shaking on coated brackets. Examples 55-56 used alumina brackets with coatings based on the ink formulations of Examples 5 and 12, respectively. Examples 57-58 used alumina brackets with coatings based on the ink formulations of Examples 6 and 10, respectively. Examples 59-60 used stainless steel brackets with coatings based on the ink formulations of Examples 6 and 10, respectively. Comparatives CE-7 and CE-8 used a CLARITY brand bracket and an ICE brand bracket, respectively. The results of the Shake Test are provided in Table 6 below.

TABLE 6

Shake Test Results

| Example/Comparative | Bracket | Coating retention after 200 cycles |
|---|---|---|
| 55 | Alumina bracket coated with Blue PVP (from Example 5) | No loss of dot coatings and slot coatings. |
| 56 | Alumina bracket coated with Blue PVP/VA (from Example 12) | No loss of dot coatings and slot coatings. |
| 57 | Alumina bracket coated with Green PVP (from Example 6) | No loss of dot coatings and slot coatings. |
| 58 | Alumina bracket coated with Green PVP/VA (from Example 10) | No loss of dot coatings and slot coatings. |
| 59 | Stainless steel bracket coated with Green PVP (from Example 6) as ID dot only | No loss of dot coatings. |
| 60 | Stainless steel bracket coated with Green PVP/VA (from Example 10) as ID dot only | No loss of dot coatings. |
| CE-7 | CLARITY brand bracket | No loss of dot coatings. |
| CE-8 | ICE brand bracket | Dot coatings and tiewing coatings remained visible. |

All of the patents and patent applications mentioned above are hereby expressly incorporated by reference. The embodiments described above are illustrative of the present invention and other constructions are also possible. Accordingly, the present invention should not be deemed limited to the embodiments described in detail above and shown in the accompanying drawings, but instead only by a fair scope of the claims that follow along with their equivalents.

What is claimed is:

1. An orthodontic appliance comprising:
   a base;
   a body extending outwardly from the base and including facial surfaces, the body having an elongated archwire slot extending in a generally mesial-distal direction;
   a water-dissolvable coating adhering to and extending over at least a portion of at least one of the tiewing facial surfaces and the archwire slot, the coating comprising:
   a colorant; and
   a water-soluble binder including at least one of a polyamide derived from monomers having an ethylenically unsaturated group, a cellulose derivative, or homopolymer/copolymer of poly(ethylene oxide),
   wherein the polyamide is selected from the group consisting of
   (i) polylactams which comprise monomers having the following functional group:

(R1)(R2)-N—C(O)—R3, where R1, R2 and R3 each are independently aliphatic or aromatic hydrocarbon moieties
   optionally substituted with one or more of N, O, and S with the understanding that R1, R2 or both may form a ring with R3 such as a pyrrolidone ring, and at least one of R1, R2, and R3 comprises a polymerizable group;
   (ii) polymers based on amides from primary amines which comprise monomers having the following functional group:

(R1)H—N—C(O)—R3 where R1 and R3 are each independently aliphatic or aromatic hydrocarbon moieties optionally substituted with one or more of N, O, and S with the understanding that R1 may form a ring with R3 such as a pyrrolidone ring, and at least one of R1 and R3 comprises a polymerizable group; and
   (iii) acrylamides which comprise monomers having the following functional group:

H2N-C(O)—R3, where R3 is as defined above,
   the cellulose derivative is selected from the group consisting of carboxymethylcellulose, hydroxypropylmethylcellulose, and hydroxyethylcellulose, and
   wherein at least 60 percent of the coating is removed when the appliance is subjected to a Dissolution Test, steps of which are:
   1) weighing 10-11 brackets to obtain the weight of coated brackets,
   2) placing the brackets on a tacky surface of a bonding prep tray and cutting the tray to fit inside a 150 milliliter beaker;
   3) placing the beaker in a shaker bath containing water at 37° C. and a circular motion of 150 rpm;
   4) adding 20 milliliters of distilled water to the beaker at t=0 covering the brackets on the tray to start dissolution;
   5) removing the brackets on the tray from water after 120 seconds, drying the brackets in an oven heated to 100° C., and weighing the brackets; and
   6) dissolving any residual coatings by rinsing the brackets with water and for coatings that are hard to be rinsed off by water, additionally sonicating the brackets in water, 5% ammonium hydroxide aqueous solution, or detergent solution to completely remove the coatings, drying the brackets, and weighing the uncoated brackets.

2. The appliance of claim 1, wherein the polyamide includes a polylactam.

3. The appliance of claim 1, wherein the colorant is a water-insoluble pigment.

4. The appliance of claim 2, wherein the polylactam comprises at least one of n-vinyl caprolactam and n-vinyl pyrrolidone.

5. The appliance of claim 4, wherein the polylactam comprises a copolymer of n-vinyl pyrrolidone and a monomer selected from: vinyl acetate, diallyldimethylammonium chloride, alkyl acrylate, styrene, methoxy polyethylene glycol acrylates, and hydroxyethylmethacrylate.

6. The appliance of claim 1, further comprising a plasticizer selected from propylene glycol, glycerol, or polyethylene glycol.

7. The appliance of claim 2, wherein the polylactam has a weight average molecular weight ranging from 15,000 to 120,000 daltons.

8. The appliance of claim 1, wherein the coating is selectively disposed in the archwire slot.

9. The appliance of claim 1, wherein the polyamide is a vinyl polymer comprising amide groups.

10. The appliance of claim 1, wherein both the base and the body are made from a translucent ceramic material.

11. The appliance of claim 1, wherein the body further comprises a vertical slot and further wherein the coating is selectively disposed in both the archwire slot and the vertical slot.

12. The appliance of claim 11, wherein at least 75 percent of the coating is removed when the appliance is subjected to the Dissolution Test.

13. The appliance of claim 12, wherein at least 85 percent of the coating is removed when the appliance is subjected to the Dissolution Test.

14. The appliance of claim 1, wherein the coating displays no bleeding after being subjected to a relative humidity of 75 percent at 40 degrees Celsius for 4 weeks.

15. A method of providing a fast dissolving and humidity-resistant marking on an orthodontic appliance having an elongated archwire slot extending in a generally mesial-distal direction thereon, the method comprising:
   compounding
   a water-insoluble pigment or water-soluble dye,
   a water-soluble binder selected from a polyamide, cellulose derivative, or homopolymer/copolymer of poly(ethylene oxide), and
   a volatile solvent to form a dispersion or solution;
   applying the dispersion or solution on a surface of the orthodontic appliance; and evaporating the volatile solvent to provide the marking, wherein the polyamide is selected from the group consisting of
(i) polylactams which comprise monomers having the following functional group:

(R1)(R2)-N—C(O)—R3, where R1, R2 and R3 each are independently aliphatic or aromatic hydrocarbon moieties optionally substituted with one or more of N, O, and S with the understanding that R1, R2 or both may form a ring with R3 such as a pyrrolidone ring, and at least one of R1, R2, and R3 comprises a polymerizable group;
(ii) polymers based on amides from primary amines which comprise monomers having the following functional group:

(R1)H—N—C(O)—R3 where R1 and R3 are each independently aliphatic or aromatic hydrocarbon moieties optionally substituted with one or more of N, O, and S with the understanding that R1 may form a ring with R3 such as a pyrrolidone ring, and at least one of R1 and R3 comprises a polymerizable group: and
(iii) acrylamides which comprise monomers having the following functional group:

H2N-C(O)—R3, where R3 is as defined above,
the cellulose derivative is selected from the group consisting of carboxymethylcellulose, hydroxypropylmethylcellulose, and hydroxyethylcellulose,
and wherein at least 60 percent of the dried coating is removed when the appliance is subjected to the Dissolution Test, the steps of which are:
1) weighing 10-11 brackets to obtain the weight of coated brackets;
2) placing the brackets on a tacky surface of a bonding prep tray and cutting the tray to fit snugly inside a 150 milliliter beaker;
3) placing the beaker in a shaker bath containing water at 37° C. and a circular motion of 150 rpm;
4) adding 20 milliliters of distilled water to the beaker at t=0 covering the brackets on the tray to start dissolution;
5) removing the brackets on the tray from water after 120 seconds, drying the brackets in an oven heated to 100° C., and weighing the brackets; and
6) dissolving any residual coatings by rinsing the brackets with water and for coatings that are hard to be rinsed off by water, additionally sonicating the brackets in water, 5% ammonium hydroxide aqueous solution, or detergent solution to completely remove the coatings, drying the brackets, and weighing the uncoated brackets.

16. The method of claim 15, wherein the polyamide comprises a polylactam.

17. The method of claim 15, wherein the cellulose derivative is selected from carboxymethylcellulose, hydroxypropylmethylcellulose, or hydroxyethylcellulose.

18. The orthodontic appliance of claim 1, wherein the coating is disposed in the archwire slot and displays no bleeding after being subjected to a relative humidity of 75 percent at 40 degrees Celsius for 4 weeks.

19. An orthodontic appliance comprising:
a base, the base having a lingual-facing surface;
a body extending outwardly from the base, the body having an elongated archwire slot extending in a generally mesial-distal direction;
a water-dissolvable coating adhering to and extending over at least a portion of the tiewing bracket facial surfaces furthest from the lingual-facing surface of the base, the coating comprising:
a colorant; and
a water-soluble binder selected from a polyamide, cellulose derivative, or homopolymer/copolymer of poly(ethylene oxide),
wherein the polyamide is selected from the group consisting of
(i) polylactams which comprise monomers having the following functional group:

(R1)(R2)-N—C(O)—R3, where R1, R2 and R3 each are independently aliphatic or aromatic hydrocarbon moieties optionally substituted with one or more of N, O, and S with the understanding that R1, R2 or both may form a ring with R3 such as a pyrrolidone ring, and at least one of R1, R2, and R3 comprises a polymerizable group;
(ii) polymers based on amides from primary amines which comprise monomers having the following functional group:

(R1)H—N—C(O)—R3 where R1 and R3 are each independently aliphatic or aromatic hydrocarbon moieties optionally substituted with one or more of N, O, and S with the understanding that R1 may form a ring with R3 such as a pyrrolidone ring, and at least one of R1 and R3 comprises a polymerizable group; and
(iii) acrylamides which comprise monomers having the following functional group:

H2N-C(O)—R3, where R3 is as defined above,
the cellulose derivative is selected from the group consisting of carboxymethylcellulose, hydroxypropylmethylcellulose, and hydroxyethylcellulose, and
wherein at least 60 percent of the dried coating is removed when the appliance is subjected to a Dissolution Test, steps of which are:
1) weighing 10-11 brackets to obtain the weight of coated brackets;
2) placing the brackets on a tacky surface of a bonding prep tray and cutting the tray to fit snugly inside a 150 milliliter beaker;
3) placing the beaker in a shaker bath containing water at 37° C. and a circular motion of 150 rpm;
4) adding 20 milliliters of distilled water to the beaker at t=0 covering the brackets on the tray to start dissolution;
5) removing the brackets on the tray from water after 120 seconds, drying the brackets in an oven heated to 100° C., and weighing the brackets;
6) dissolving any residual coatings by rinsing the brackets with water and for coatings that are hard to be rinsed off by water, additionally sonicating the brackets in water, 5% ammonium hydroxide aqueous solution, or detergent solution to completely remove the coatings, drying the brackets, and weighing the uncoated brackets.

20. The appliance of claim 19, wherein the polyamide is derived from monomers having an ethylenically unsaturated group.

* * * * *

UNITED STATES PATENT AND TRADEMARK OFFICE
CERTIFICATE OF CORRECTION

PATENT NO. : 10,307,224 B2
APPLICATION NO. : 14/240455
DATED : June 4, 2019
INVENTOR(S) : Tsi-Zong Tzou et al.

Page 1 of 1

It is certified that error appears in the above-identified patent and that said Letters Patent is hereby corrected as shown below:

In the Specification

<u>Column 6</u>
Line 43 (approx.), delete "(DMAEMA)" and insert -- (DMAPMA) --, therefor.

<u>Column 6</u>
Line 49 (approx.), after "Germany)" insert -- . --.

<u>Column 9</u>
Line 58, delete "Inc.," and insert -- Inc.; --, therefor.

Signed and Sealed this
Seventeenth Day of March, 2020

Andrei Iancu
*Director of the United States Patent and Trademark Office*